United States Patent
Bourne et al.

(10) Patent No.: US 8,291,933 B2
(45) Date of Patent: Oct. 23, 2012

(54) SPRING-LESS CHECK VALVE FOR A HANDPIECE

(75) Inventors: John M. Bourne, Tustin, CA (US); Guangyao Jia, Irvine, CA (US); Glenn Sussman, Laguna Nigel, CA (US)

(73) Assignee: Novartis AG, Basel (CH)

( * ) Notice: Subject to any disclaimer, the term of this patent is extended or adjusted under 35 U.S.C. 154(b) by 961 days.

(21) Appl. No.: 12/237,468

(22) Filed: Sep. 25, 2008

(65) Prior Publication Data

US 2010/0076471 A1   Mar. 25, 2010

(51) Int. Cl.
    *F16K 15/04* (2006.01)
(52) U.S. Cl. .................................. 137/533.11; 606/107
(58) Field of Classification Search ............. 137/533.11, 137/533.13, 533.19, 539, 512.1; 606/107
    See application file for complete search history.

(56) References Cited

U.S. PATENT DOCUMENTS

| | | | |
|---|---|---|---|
| 121,697 A | 12/1871 | Wheatland | |
| 294,334 A | 2/1884 | Reed et al. | |
| 351,159 A | 10/1886 | Brengel | |
| 865,631 A | 9/1907 | Cotter | |
| 2,121,936 A | 6/1938 | Thomas | |
| 2,386,765 A * | 10/1945 | Adams et al. | 123/574 |
| 2,536,836 A | 1/1951 | Bowling | |
| 2,623,725 A | 12/1952 | Sands | |
| 2,755,816 A * | 7/1956 | Collins | 137/496 |
| 3,085,589 A | 4/1963 | Sands | |
| 3,191,807 A | 6/1965 | Rodrigues | |
| 3,336,942 A | 8/1967 | Keith et al. | |
| 3,561,471 A | 2/1971 | Sands | |
| 3,589,363 A | 6/1971 | Banko et al. | |
| 3,693,613 A | 9/1972 | Kelman | |
| 3,756,270 A | 9/1973 | Fonseca et al. | |
| 3,818,913 A | 6/1974 | Wallach | |
| 4,018,247 A | 4/1977 | Carr | |
| 4,030,520 A | 6/1977 | Sands | |
| 4,095,580 A | 6/1978 | Murray et al. | |
| 4,155,374 A | 5/1979 | Diehl | |
| 4,156,187 A | 5/1979 | Murry et al. | |
| 4,168,707 A | 9/1979 | Douvas et al. | |
| 4,223,676 A | 9/1980 | Wuchinich et al. | |
| 4,229,149 A * | 10/1980 | Turner | 417/554 |

(Continued)

FOREIGN PATENT DOCUMENTS

EP   1199054 A1   4/2002

(Continued)

OTHER PUBLICATIONS

International Searching Authority, Written Opinion of the International Searching Authority, PCT/US2009/057675, Mar. 25, 2011, 5 pages.

*Primary Examiner* — Kevin Lee
*Assistant Examiner* — Macade Brown (57) ABSTRACT

A hand piece for a surgical instrument is provided. The handpiece has an inlet, a chamber (with upstream and downstream portions), a flow control member, a pulse engine, and an outlet. The inlet communicates with the upstream portion of the chamber. The downstream portion of the chamber communicates with the engine. The engine communicates with the outlet. In a closed position of the member, flow from the inlet moves the member to the open position thereby allowing flow through the flow path. In the open position, pulses from the engine move the member to the closed position before pulses from the pulse engine can flow through the flow path, thereby preventing flow through the flow path.

17 Claims, 5 Drawing Sheets

U.S. PATENT DOCUMENTS

| | | | |
|---|---|---|---|
| 4,246,902 A | 1/1981 | Martinez |
| 4,274,411 A | 6/1981 | Dotson, Jr. |
| 4,380,911 A | 4/1983 | Zumbiel |
| 4,493,694 A | 1/1985 | Wuchinich |
| 4,515,583 A | 5/1985 | Sorich |
| 4,570,669 A | 2/1986 | Pauliukonis |
| 4,589,415 A | 5/1986 | Haaga |
| 4,609,368 A | 9/1986 | Dotson, Jr. |
| 4,655,247 A | 4/1987 | Westra et al. |
| 4,657,490 A | 4/1987 | Abbott |
| 4,668,231 A | 5/1987 | deVries et al. |
| 4,784,652 A | 11/1988 | Wikstrom |
| 4,797,098 A | 1/1989 | Kawata |
| 4,869,715 A | 9/1989 | Sherburne |
| 4,909,783 A | 3/1990 | Morrison |
| 4,921,477 A | 5/1990 | Davis |
| 4,922,902 A | 5/1990 | Wuchinich et al. |
| 4,935,005 A | 6/1990 | Haines |
| 4,989,583 A | 2/1991 | Hood |
| 5,061,241 A | 10/1991 | Stephens et al. |
| 5,152,753 A | 10/1992 | Laguette et al. |
| 5,154,694 A | 10/1992 | Kelman |
| 5,261,883 A | 11/1993 | Hood et al. |
| 5,322,504 A | 6/1994 | Doherty et al. |
| 5,358,150 A | 10/1994 | Scheuble et al. |
| 5,359,996 A | 11/1994 | Hood |
| 5,380,280 A | 1/1995 | Peterson |
| 5,514,088 A | 5/1996 | Zakko |
| 5,514,110 A | 5/1996 | Teh |
| 5,562,692 A | 10/1996 | Bair |
| 5,577,533 A | 11/1996 | Cook, Jr. |
| 5,580,347 A | 12/1996 | Reimels |
| 5,616,120 A | 4/1997 | Andrew et al. |
| 5,735,815 A | 4/1998 | Bair |
| 5,741,229 A | 4/1998 | Robinson et al. |
| 5,853,384 A | 12/1998 | Bair |
| 5,865,790 A | 2/1999 | Bair |
| 5,885,243 A | 3/1999 | Capetan et al. |
| 5,989,212 A | 11/1999 | Sussman et al. |
| 5,997,499 A | 12/1999 | Sussman et al. |
| 6,004,284 A | 12/1999 | Sussman et al. |
| 6,080,128 A | 6/2000 | Sussman et al. |
| 6,110,162 A | 8/2000 | Sussman et al. |
| 6,123,101 A | 9/2000 | Velie et al. |
| 6,155,975 A | 12/2000 | Urich et al. |
| 6,179,805 B1 | 1/2001 | Sussman et al. |
| 6,179,808 B1 | 1/2001 | Boukhny et al. |
| 6,186,148 B1 | 2/2001 | Okada |
| 6,196,989 B1 | 3/2001 | Padget et al. |
| 6,206,848 B1 | 3/2001 | Sussman et al. |
| 6,241,700 B1 | 6/2001 | Leukanech |
| 6,258,111 B1 | 7/2001 | Ross et al. |
| 6,287,274 B1 | 9/2001 | Sussman et al. |
| 6,315,755 B1 | 11/2001 | Sussman |
| 6,331,171 B1 | 12/2001 | Cohen |
| 6,398,759 B1 | 6/2002 | Sussman et al. |
| 6,425,883 B1 | 7/2002 | Urich et al. |
| 6,440,103 B1 | 8/2002 | Hood et al. |
| 6,513,545 B2 | 2/2003 | Rhone et al. |
| 6,575,929 B2 | 6/2003 | Sussman et al. |
| 6,575,990 B1 | 6/2003 | Wang et al. |
| 6,579,270 B2 | 6/2003 | Sussman et al. |
| 6,589,201 B1 | 7/2003 | Sussman et al. |
| 6,589,204 B1 | 7/2003 | Sussman et al. |
| 6,623,477 B1 | 9/2003 | Elbrecht et al. |
| 6,648,847 B2 | 11/2003 | Sussman et al. |
| 6,676,628 B2 | 1/2004 | Sussman et al. |
| 6,796,957 B2 | 9/2004 | Carpenter et al. |
| 6,830,064 B2 | 12/2004 | Ji |
| 6,860,868 B1 | 3/2005 | Sussman et al. |
| 6,892,756 B2 | 5/2005 | Schulze |
| 6,920,895 B2 | 7/2005 | Avis et al. |
| 6,921,385 B2 | 7/2005 | Clements et al. |
| 6,953,052 B2 | 10/2005 | Lehtonen |
| 7,160,268 B2 | 1/2007 | Darnell et al. |
| 7,509,831 B2 | 3/2009 | Khashayar |
| 7,535,815 B2 | 5/2009 | Van Den Homberg et al. |
| 7,789,069 B2 * | 9/2010 | Rodriguez-Amaya et al. ............ 123/446 |
| 2002/0013572 A1 | 1/2002 | Berlin |
| 2002/0161326 A1 | 10/2002 | Sussman et al. |
| 2002/0188261 A1 | 12/2002 | Hruska |
| 2003/0195538 A1 | 10/2003 | Wang et al. |
| 2004/0024380 A1 | 2/2004 | Darnell et al. |
| 2004/0082939 A1 | 4/2004 | Berlin |
| 2005/0228423 A1 | 10/2005 | Khashayar et al. |
| 2005/0228424 A1 | 10/2005 | Khashayar et al. |
| 2006/0058823 A1 | 3/2006 | Dimalanta et al. |
| 2006/0161101 A1 * | 7/2006 | Dimalanta et al. ............ 604/67 |
| 2006/0173403 A1 | 8/2006 | Injev |
| 2006/0184091 A1 | 8/2006 | Dimalanta et al. |
| 2006/0212037 A1 * | 9/2006 | Sussman et al. ............ 606/107 |
| 2006/0212039 A1 | 9/2006 | Sussman et al. |
| 2006/0224116 A1 | 10/2006 | Underwood et al. |
| 2008/0073906 A1 | 3/2008 | Turner |
| 2008/0077077 A1 | 3/2008 | Williams |
| 2008/0082077 A1 | 4/2008 | Williams |
| 2008/0086093 A1 | 4/2008 | Steppe et al. |
| 2008/0125697 A1 | 5/2008 | Gao |
| 2009/0032121 A1 | 2/2009 | Chon |
| 2009/0032123 A1 | 2/2009 | Bourne |
| 2009/0068870 A1 | 3/2009 | Mezhinsky |

FOREIGN PATENT DOCUMENTS

| | | |
|---|---|---|
| WO | WO 2006/101727 A2 | 9/2006 |
| WO | WO 2006/101727 A3 | 9/2006 |
| WO | WO 2010/036610 A1 | 4/2010 |

* cited by examiner

SPRING-LESS CHECK VALVE FOR A HANDPIECE

BACKGROUND OF THE INVENTION

This invention relates generally to the field of opthalmologic surgery and more particularly to apparatus and methods for practicing liquefaction techniques of cataract removal.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age, disease, trauma, etc. causes the lens to become less transparent, vision deteriorates because of the diminished light which can be transmitted to the retina. This deficiency in the lens of the eye is medically known as a cataract. A generally accepted treatment for this condition is surgical removal and replacement of the lens with an artificial intraocular lens (IOL).

SUMMARY OF THE INVENTION

Embodiments of the present disclosure provide apparatus and methods for opthalmologic surgery that eliminate, or at least substantially reduce, the shortcomings of previously available apparatus and methods for opthalmologic surgery.

In one embodiment, a handpiece for practicing opthalmologic procedures is provided. A body of the handpiece can be utilized to guide a surgical cutting tip. The handpiece can include an inlet port, a flow control member, a pulse engine, and an outlet port. Additionally, the handpiece can define a first flow path and a chamber with an upstream portion and a downstream portion. The inlet port can communicate with the chamber which can communicate with the pulse engine. From there, the pulse engine can communicate with the outlet port. The flow control member can move between open and closed positions wherein, in the closed position, flow from the inlet port can move the flow control member to the open position, thereby allowing flow through the first flow path. In the open position, a pressure increase from the pulse engine, and traveling along a second flow path to the flow control member, can move the flow control member to the closed position before the pressure increase can travel through the first flow path, thereby preventing flow through the first flow path.

In some embodiments, the flow control member can be a sphere. An insert of the handpiece can define the chamber and at least a portion of the flow path. The first flow path can include a restriction which operates to retard flow through the first flow path while the flow control member moves from the open to the closed position. In some embodiments, the open and closed positions of the flow control member can be about 0.001" to about 0.010" (or, in some embodiments, about 0.002" to about 0.003") apart.

Embodiments provide advantages over previously available handpieces. Various embodiments provide handpiece check valves which can crack open substantially without an applied positive differential pressure. Embodiments provide check valves with fewer moving parts than previously available. Hence, embodiments provide handpieces with higher reliability than previously available handpieces.

These, and other, aspects will be better appreciated and understood when considered in conjunction with the following description and the accompanying drawings. The following description, while indicating various embodiments and numerous specific details thereof, is given by way of illustration and not of limitation. Many substitutions, modifications, additions or rearrangements may be made within the scope of the disclosure, and the disclosure includes all such substitutions, modifications, additions or rearrangements.

BRIEF DESCRIPTION OF THE FIGURES

A more complete understanding of the disclosure and the advantages thereof may be acquired by referring to the following description, taken in conjunction with the accompanying drawings in which like reference numbers generally indicate like features and wherein.

DETAILED DESCRIPTION

Various embodiments of the disclosure are illustrated in the FIGURES, like numerals being generally used to refer to like and corresponding parts of the various drawings. Embodiments of the disclosure provide apparatus and methods for cataract extraction.

As used herein, the terms "comprises," "comprising," "includes," "including," "has," "having" or any other variation thereof, are intended to cover a non-exclusive inclusion. For example, a process, process, article, or apparatus that comprises a list of elements is not necessarily limited only those elements but may include other elements not expressly listed or inherent to such process, process, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of, any term or terms with which they are utilized. Instead, these examples or illustrations are to be regarded as being described with respect to one particular embodiment and as illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example", "for instance", "e.g.", "in one embodiment".

Many lenses affected by cataracts are removed by a surgical technique called phacoemulsification. During this procedure, in some embodiments, a thin phacoemulsification cutting tip can be inserted into the diseased lens and vibrated ultrasonically. The vibrating cutting tip liquefies or emulsifies the lens so that the lens may be aspirated out of the eye. The diseased lens, once removed, can be replaced by an artificial lens.

A typical ultrasonic surgical device suitable for opthalmologic procedures consists of an ultrasonically driven handpiece, an attached cutting tip, irrigating sleeve, and an electronic control console in some embodiments. The handpiece assembly can be attached to the control console by an electric cable and flexible tubes. Through the electric cable, the console can vary the power level transmitted by the handpiece to the attached cutting tip and the flexible tubes can supply irrigation fluid to, and draw aspiration fluid from, the eye through the handpiece assembly.

The operative part of the handpiece can be a centrally located, hollow resonating bar or horn directly attached to a set of piezoelectric crystals. The crystals can supply the required ultrasonic vibration needed to drive both the horn and the attached cutting tip during phacoemulsification and can be controlled by the console. The crystal/horn assembly can be suspended within the hollow body or shell of the handpiece by flexible mountings. In some embodiments, the handpiece body terminates in a reduced diameter portion or nosecone at the body's distal end. The nosecone can be externally threaded to accept the irrigation sleeve. In some embodiments, the horn bore is internally threaded at its distal end to receive the external threads of the cutting tip. The irrigation sleeve can have an internally threaded bore that is screwed onto the external threads of the nosecone. The cutting tip can be adjusted so that the tip projects only a predetermined amount past the open end of the irrigating sleeve.

In various embodiments, the ends of the cutting tip and irrigating sleeve can be inserted into a small incision of predetermined width in the cornea, sclera, or other location. The cutting tip can be ultrasonically vibrated along its longitudinal axis within the irrigating sleeve by the crystal-driven ultrasonic horn, thereby emulsifying the selected tissue in situ. The hollow bore of the cutting tip can communicate with the bore in the horn that in turn communicates with the aspiration line from the handpiece to the console. A reduced pressure or vacuum source in the console draws or can aspirate the emulsified tissue from the eye through the open end of the cutting tip, the cutting tip and horn bores and the aspiration line and into a collection device. The aspiration of emulsified tissue can be aided by a saline flushing solution or irrigant that is injected into the surgical site through the small annular gap between the inside surface of the irrigating sleeve and the cutting tip.

In some embodiments, a cataract removal method is provided that can involve the injection of warm (approximately 45 degree Celsius to 105.degree Celsius) water or saline to liquefy or gellate the hard lens nucleus, thereby making it possible to aspirate the liquefied lens from the eye. Aspiration can be conducted concurrently with the injection of the heated solution and the injection of a relatively cool solution, thereby quickly cooling and removing the heated solution. In some embodiments, the apparatus, however, heats the solution separately from the surgical handpiece. Apparatus and methods for practicing cataract extraction using various liquefaction apparatus and techniques are disclosed in U.S. patent application Ser. No. 11/037,062, entitled Surgical System and Handpiece, by Dimalanta et al. and in U.S. Pat. No. 5,616,120, entitled Method And Apparatus For Lenticular Liquefaction And Aspiration, by Andrew et al. both of which are incorporated herein as if set forth in full.

Recently, a device was commercially introduced for practicing liquefaction techniques. The AQUALASE® handpiece, part of the INFINITI® Vision System available from Alcon Laboratories, Inc., Fort Worth, Tex., produces pulses of warmed irrigation fluid for lens removal and cortical cleanup. Embodiments disclosed herein can be used in conjunction with the AQUALASE, or other, handpieces.

Figure 1:
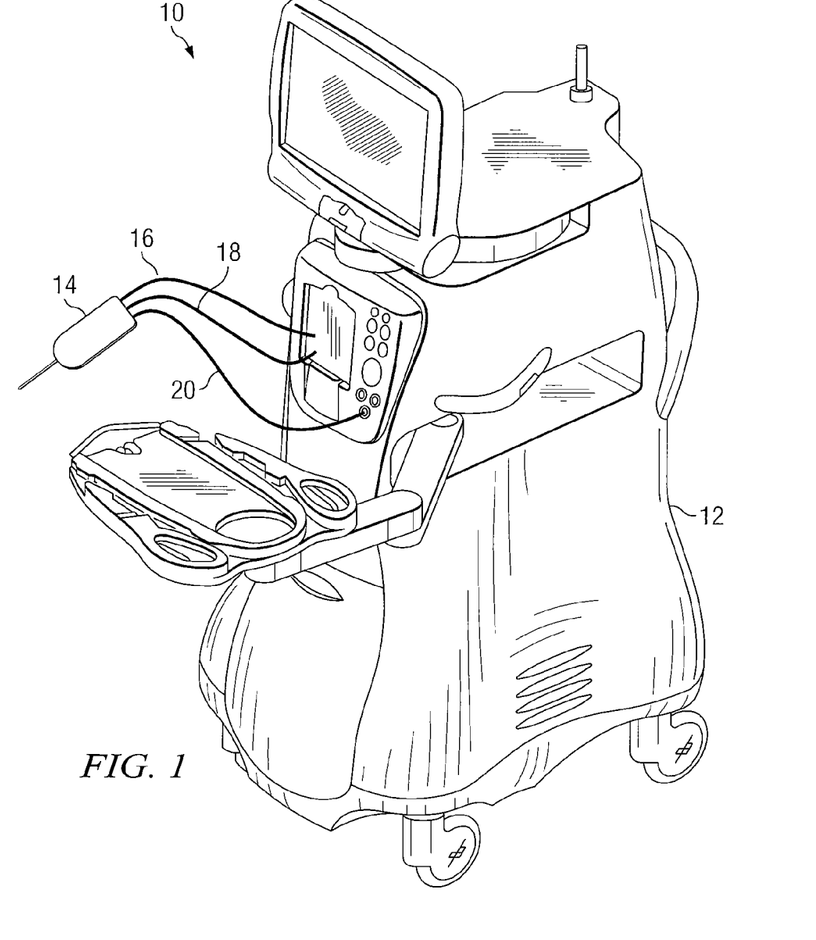
FIG. 1 illustrates a perspective view of one embodiment of a surgical system.

As illustrated in FIG. 1, system 10 can include one embodiment of control console 12 and handpiece 14. System 10 may be any suitable system, such as the INFINITI®. Vision System available from Alcon Laboratories, Inc., Fort Worth, Tex. Handpiece 14 may be any suitable handpiece, such as the AQUALASE® handpiece available from Alcon Laboratories, Inc., Fort Worth, Tex. System 10 can be connected to console 12 by fluid tubes 16 and 18, and electrically connected to console 12 by electrical cable 20. Control console 12 can contain appropriate hardware and software (not shown, but well-known in the art) for providing control signals to handpiece 14.

Figure 2:
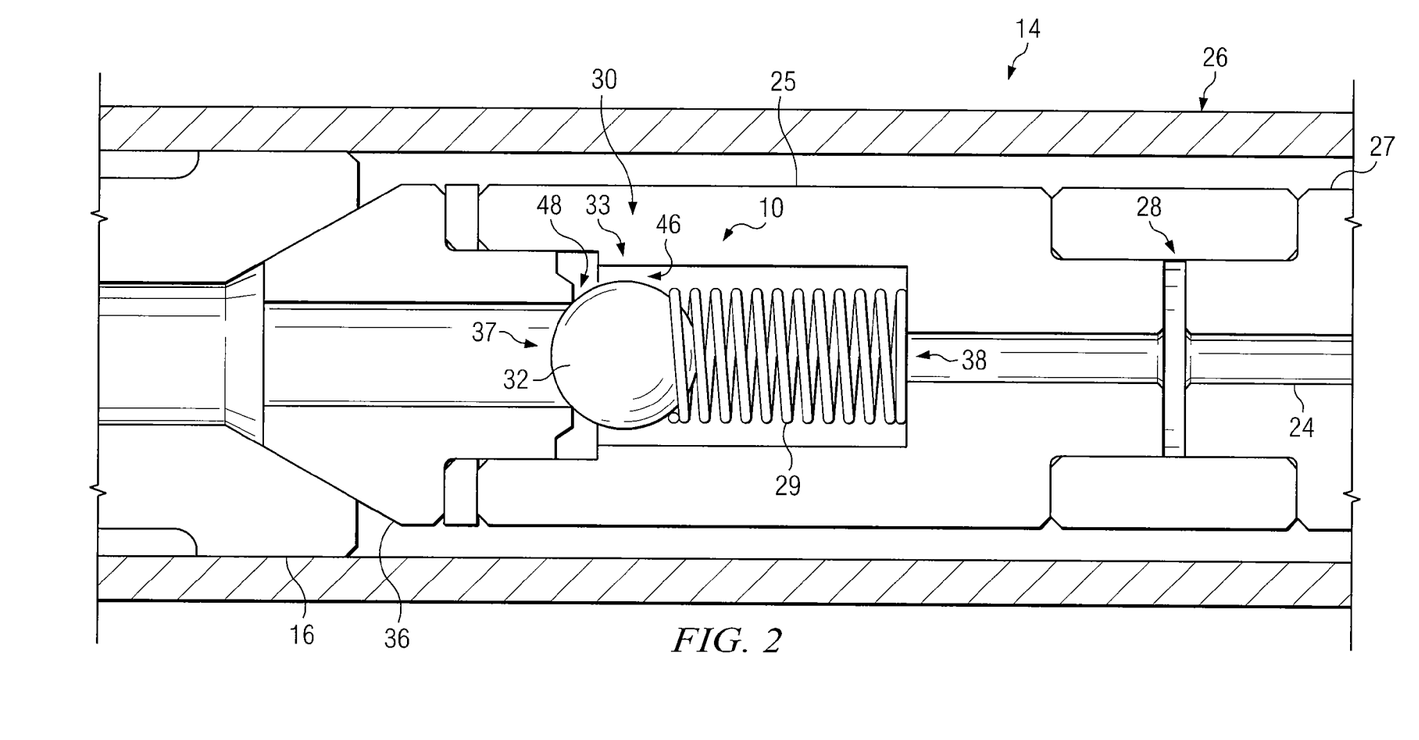
FIG. 2 illustrates a cross sectional view of one embodiment of a handpiece.

As illustrated in FIG. 2, embodiments of handpieces 14 for practicing liquefaction techniques generally can include an aspiration line (connected to console 12 through tubing 18) and irrigation line 24 (connected to console 12 by tubing 16). Irrigation line 24 can provide sterile irrigation fluid to pulse engine 26. Pulse engine 26 can contain proximal electrode 25 and distal electrode 27 to form boiling chamber 28 that produces pressurized pulses of irrigation fluid. Irrigation fluid boiled in chamber 28 can exit pulse engine 26 through irrigation line 24. The pressure of the pulse exiting pulse engine 26 through irrigation line 24 can be determined by the size and duration of the electrical drive signal sent to pulse engine 26 through cable 20 by console 12.

As illustrated in FIG. 2, one embodiment of handpiece 14 includes check valve 30 with spring 29 and flow control member 32 which can bias check valve 30 closed. Handpiece 14 can define valve chamber 33 in which check valve 30 can fit. Check valve 30 can open when some positive differential pressure (a "cracking pressure") is applied across it. More specifically, a source of irrigation fluid (for instance, balanced saline solution (BSS)) in communication with handpiece 14 can supply sufficient pressure to urge flow control member 32 downstream from closed seat 48 (against the biasing force of spring 29), thereby opening check valve 30. Thus, the irrigation fluid can flow past closed seat 48 from tube 16 to irrigation line 24 through upstream chamber portion 37 (which can connect tube 16 to check valve 32), flow path 46 (which can carry the BSS around flow control member 32), and downstream chamber portion 38.

Figure 3:
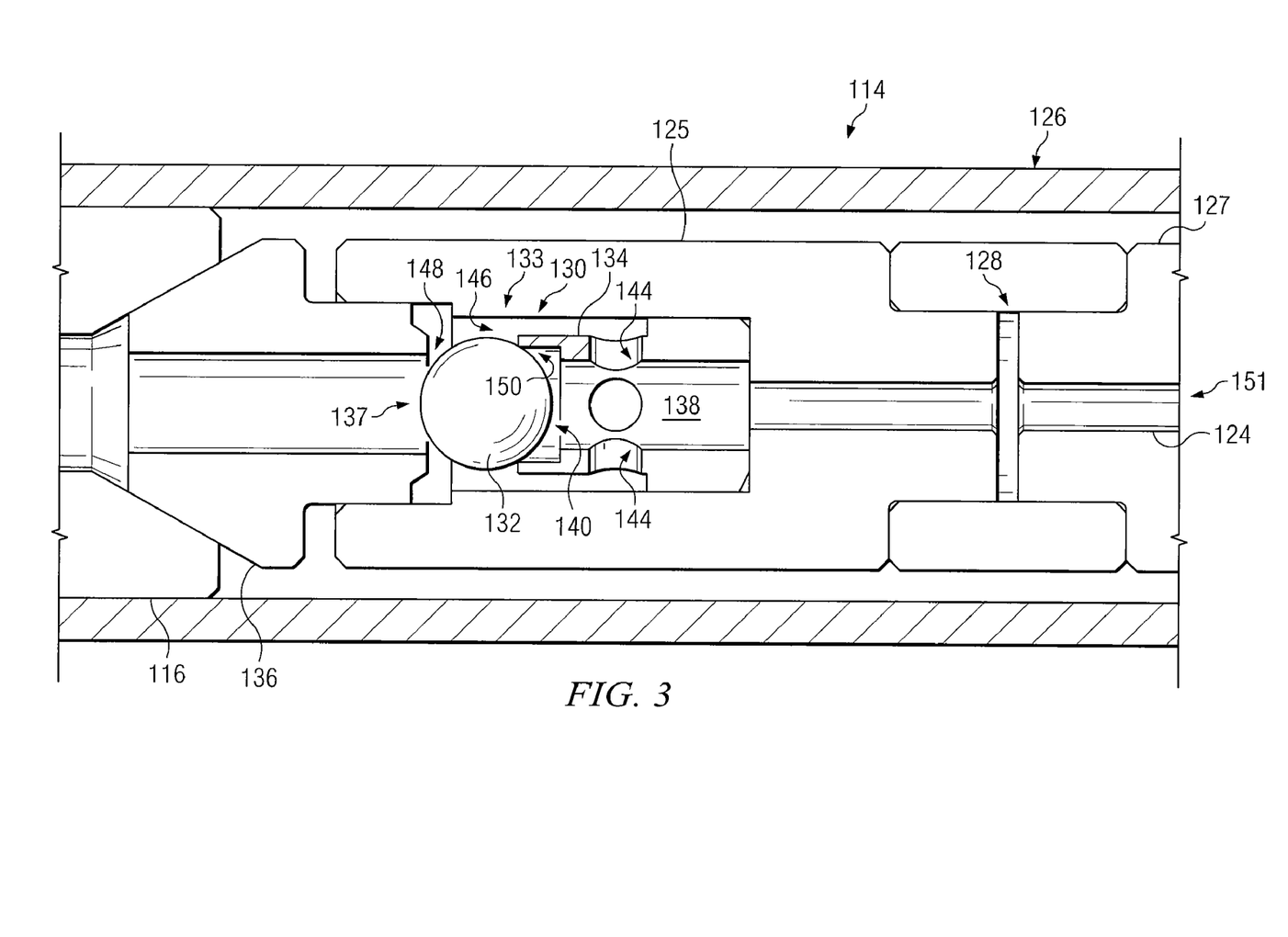
FIG. 3 illustrates a cross sectional view of one embodiment of a handpiece.

With reference now to FIG. 3, one embodiment of handpiece 114 is illustrated in its open position. In some embodiments, handpiece 114 can include check valve 130 as illustrated by FIG. 3. Check valve 130 can "crack" (open) substantially without a differential pressure being applied across it, thereby obviating the need for a source of pressure (such as a bag(s) of irrigation fluid). Moreover, check valve 130 can close when pressure increases from pulse engine 128 reach it without including a spring or other biasing member. More particularly, handpiece 114 can include pulse engine 126 with proximal electrode 125 and distal electrode 127 (which form boiling chamber 128 and define irrigation line 124), check valve 130, flow control member 132, valve chamber 133, insert 134, tube adaptor 136, upstream chamber portion 137, downstream chamber portion 138, socket 140, apertures 144, flow path 146, closed seat 148, open seat 150, and outlet port 151. Flow control member 132 and insert 134 can cooperate to allow flow through flow path 146 when pulse engine 126 is not generating a pulse of irrigation fluid. Flow control member 132 and insert 134 can cooperate to prevent flow through flow path 146 when pulse engine 126 is generating a pulse of irrigation fluid. In some embodiments, flow control member 132 and insert 134 can be shaped and dimensioned to fit within the volume provided for check valve 30 and spring 29 (see FIG. 2).

With continuing reference to FIG. 3, tube adapter 136 can be shaped and dimensioned so that (in conjunction with flow control member 132, insert 134, and various features of handpiece 114) tube adapter 136 can hold components 116 and 132 in operative relationship to each other (as will be described with more specificity herein). At its proximal end, tube adapter 136 can be adapted to receive and retain irrigation tube 116. Proximal electrode 125 can define an inlet port adjacent to upstream chamber portion 137 of valve chamber 133. At its distal end, tube adapter 136 can be shaped and dimensioned to fit within the inlet port of proximal electrode 125. Various features of proximal electrode 125 can retain tube adapter 136 in the inlet port.

Figure 6:
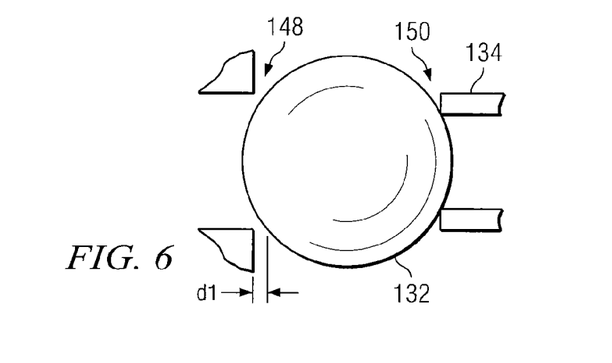
FIG. 6 illustrates a cross sectional view of one embodiment of a flow control member.

Flow control member 132 can determine, by its position, whether check valve 130 is open or closed. Flow control member 132 can be positioned in valve chamber 133 toward upstream chamber portion 137 and generally adjacent to tube adaptor 136. In the open position shown in FIG. 3, flow control member 132 can be distance d1 (see FIG. 6) downstream of tube adaptor 136 and can abut open seat 150. Open seat 150 and flow control member 132 can be shaped and dimensioned in such a manner to align flow control member 132 with open seat 150, thereby improving closing speed and efficiency. In the closed position, flow control member 132 can abut closed seat 148 on the distal end of tube adaptor 136. Thus, flow control member 132 is movable between open and closed positions. Distance d1 between flow control member's 132 open and closed positions can be about 0.001" to about 0.010" for a handpiece 114 shaped and dimensioned to be grasp by surgical personnel. In some embodiments, distance d1 can be about 0.002" to about 0.003". Flow control member 132 can be spherical and can partially fit in socket 140 of insert 134. As shown in FIG. 3, a sector of about 120 degrees of a particular spherical flow control member 132 can fit in socket 140.

Flow path 146 from upstream chamber portion 137 to downstream portion 138 can be formed in proximal electrode 125 as an annulus around flow control member 132 and around an upstream portion of insert 134. Flow path 146 can communicate with apertures 144 positioned about the circumference of insert 134 and (through apertures 144) with downstream chamber portion 138.

Insert 134 can be generally adjacent to and downstream from flow control member 132. Insert 134 (together with flow control member 132) can be shaped and dimensioned to fit within valve chamber 133. Insert 134 can be generally cylindrical and can define apertures 144, socket 140, and downstream chamber portion 138. Downstream chamber portion 138 can allow communication from irrigation line 124 to flow control member 132, apertures 144, and flow path 146. Thus, in the open position shown in FIG. 3, check valve 130 can allow flow passing over flow control member 132 and closed seat 148, from irrigation tube 116 to outlet port 151 through tube adaptor 136, flow path 146, apertures 144, downstream chamber portion 138, boiling chamber 128 and irrigation line 124.

Figure 4:
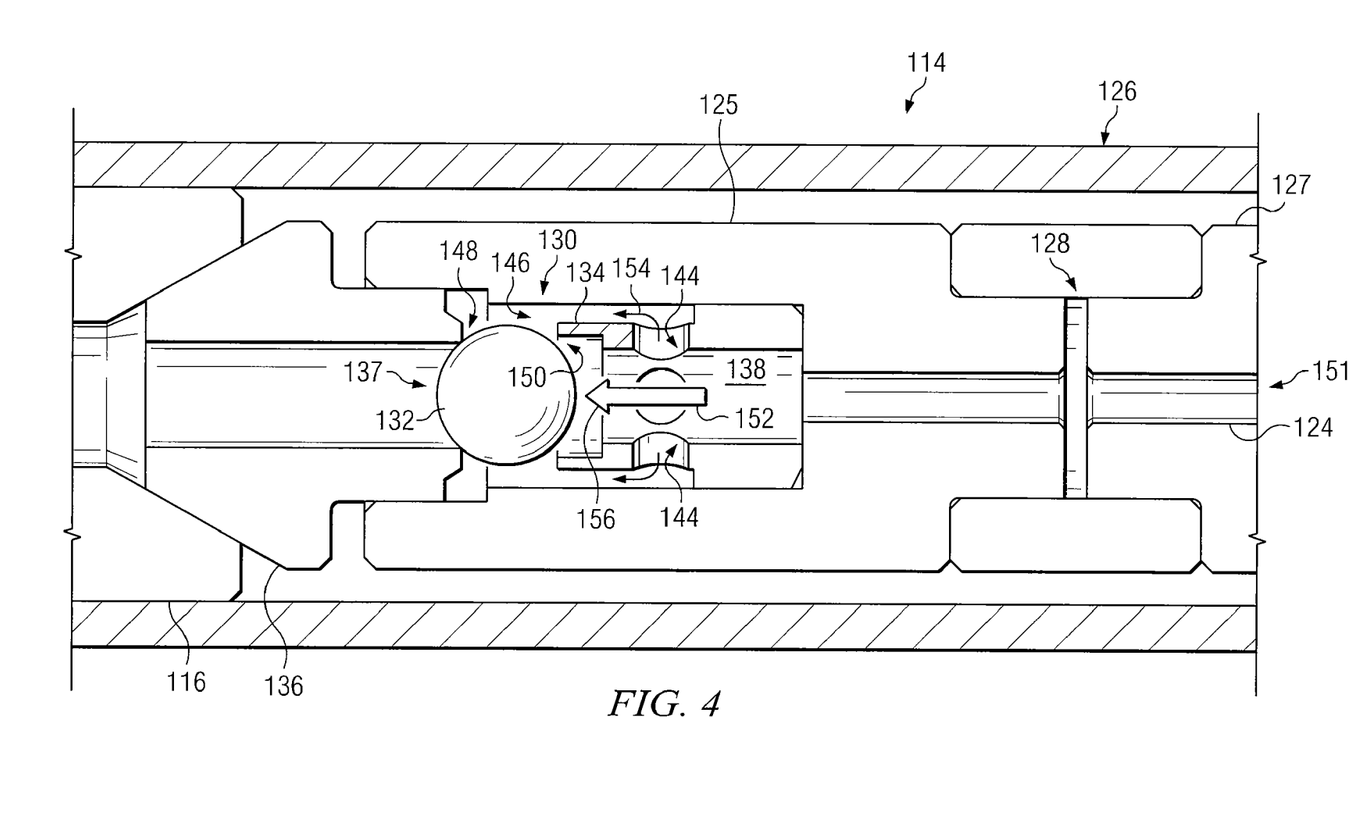
FIG. 4 illustrates a cross sectional view of one embodiment of a handpiece.

In the closed position shown by FIG. 4, flow control member 132 can abut closed seat 148, thereby preventing communication between upper chamber portion 137 and flow path 146. Flow control member 132 can be generally adjacent to, but spaced apart from open seat 150 by distance d1 when in the closed position. Thus, communication can be allowed from boiling chamber 128, through downstream chamber portion 138, through apertures 144, and into flow path 146. Communication from boiling chamber 128 to the downstream side of flow control member 132 can be allowed via irrigation line 124, downstream chamber portion 138, and socket 140. Flow from flow path 146 passing over closed seat 148 and flow control member 132, and into upstream chamber portion 137 can be prevented by flow control member 132 in the closed position.

When in the open position illustrated by FIG. 3, flow control member 132 can be moved to the closed position illustrated by FIG. 4 as follows. When boiling chamber 128 creates pulse 152 (see FIG. 4) of warm irrigation fluid, pulse 152 from boiling chamber 128 can communicate through irrigation line 124 both upstream and downstream from boiling chamber 128. Pulse 152 can communicate through downstream chamber portion 138 to the vicinity of apertures 144. Near apertures 144, pulse 152 can split with pulse portion 154 communicating through apertures 144 to flow path 146. Another pulse portion 156 of pulse 152 can continue moving through downstream chamber portion 138 toward socket 140 and flow control member 132.

Because downstream chamber portion 138 can be relatively unobstructed with few, if any, flow retarding features, pulse portion 156 can reach flow control member 132 relatively rapidly. At the downstream side of flow control member 132, pulse portion 156 can urge flow control member 132 away from open seat 150 and toward closed seat 148 across distance d1 (see FIG. 6). At some time, flow control member 132 can reach closed seat 148, thereby preventing communication from flow path 146 to upper chamber portion 137.

In the meantime, pulse portion 154 (which communicated through apertures 144) can be communicating upstream through flow path 146. As pulse portion 154 communicates upstream, flow-retarding features it encounters can retard its speed. For instance, pulse portion 154 can turn at least twice (once in downstream chamber portion 138 to reach apertures 144 and once upstream of apertures 144 to turn into flow path 146). Aperture 144 can be sharp edged thereby retarding communication of pulse portion 154 due to orifice effects of apertures 144. Flow path 146 can be a relatively narrow annulus between proximal electrode 125 and insert 134, thereby retarding pulse portion 154 communication along flow path 146. Narrowing of flow path 146 between flow control member 132 and proximal electrode 125 can retard communication of pulse portion 154 also. In some embodiments, pulse portion 154 passing flow control member 132 can turn toward open seat 150, thereby further retarding communication of pulse portion 154.

As a result, in some embodiments, by the time pulse portion 154 reaches closed seat 148, flow control member 132 can be substantially in its closed position abutting and sealing against closed seat 148. Accordingly, backflow (if any) through closed seat 148 can be minimal. As a result, substantially all of pulse 152 from boiling chamber 128 can be directed downstream and out of outlet port 151 at some time. For instance, pulse portion 156 (which communicated upstream) can reflect from check valve 130 and subsequently communicate out of output port 151 through irrigation line 124. Substantially all of pulse 152 may therefore be directed at tissue which surgical personnel may wish to liquefy and extract. In some embodiments, irrigation line 124, boiling chamber 128, flow control member 132, downstream chamber portion 138, socket 140, apertures 144, flow path 146, closed seat 148, and open seat 150 can be shaped and dimensioned as a fluid system to select a time-varying profile of pulse 152 communicating to the distal end of irrigation line 124.

With continuing reference to FIGS. 3 and 4, flow control member 132 and insert 134 can be shaped and dimensioned to fit within the volume occupied by check valve 30 including spring 29 (see FIG. 2). Thus, in some embodiments, handpieces 14 of FIG. 2 can be converted to include check valves 130 (without springs 29 or other biasing members). More particularly, handpiece 14 can be converted by removing the ball and spring 29 of check valve 30 from handpiece 14 and inserting insert 134 into handpiece 14 with socket 140 pointing toward the proximal end of handpiece 14. Flow control member 132 can be inserted into handpiece 14 and socket 140 (of insert 134). Tube adapter 136 can be inserted into valve handpiece 14 to enclose check valve 130 in handpiece 14 (converted to include spring-less check valve 130).

Figure 5:
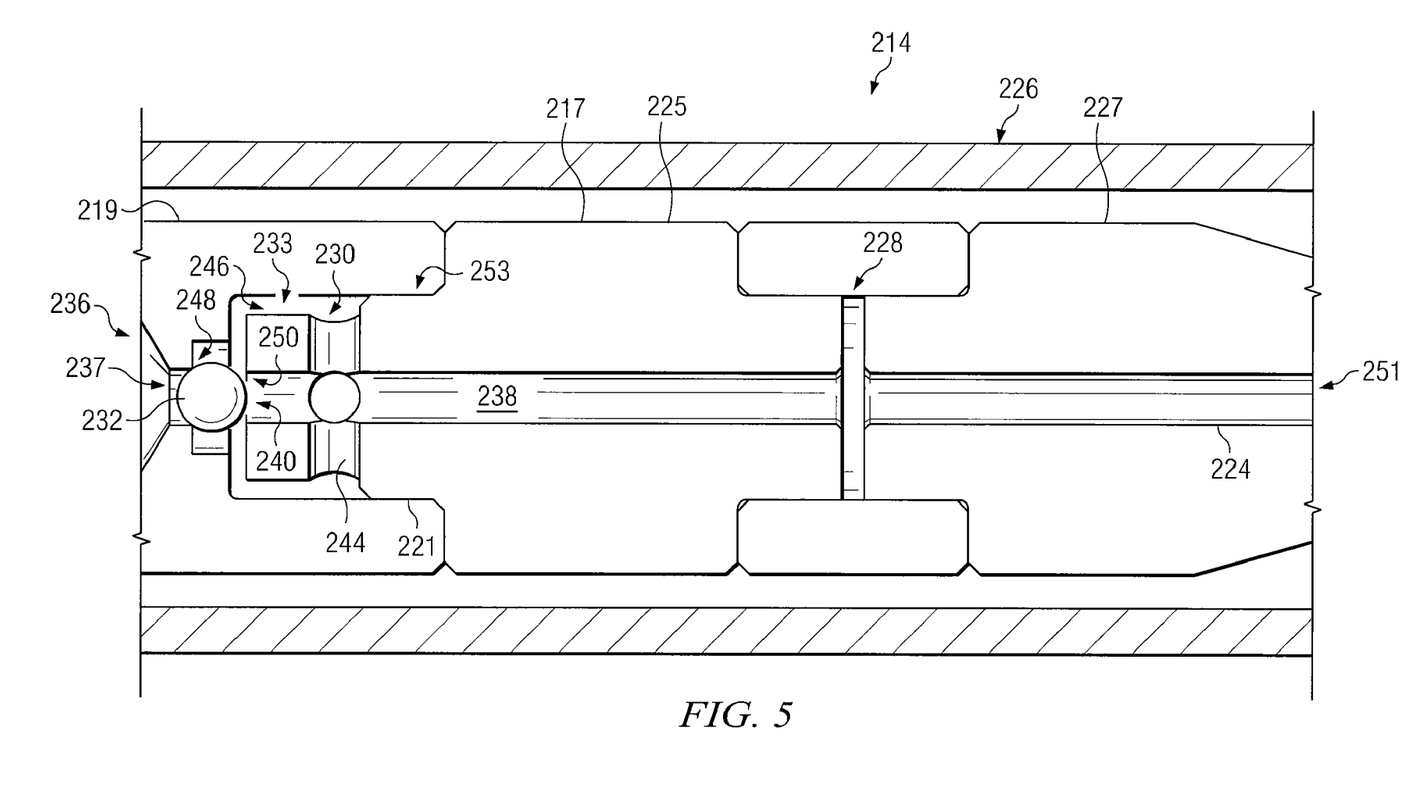
FIG. 5 illustrates a cross sectional view of one embodiment of a handpiece.

With reference now to FIG. 5, one embodiment of handpiece 214 is illustrated. Handpiece 214 can include pulse engine electrodes 225 and 227, handpiece cap 219, pulse engine projection 221, irrigation line 224, pulse engine 226, boiling chamber 228, check valve 230, flow control member 232, inlet port 236, upstream chamber portion 237, downstream chamber portion 238, socket 240, apertures 244, flow path 246, closed seat 248, open seat 250, and outlet port 251. Handpiece cap 219 can define upstream chamber portion 237 and closed seat 248. Handpiece body 214 can include pulse engine projection 221 extending from its distal end. Pulse engine projection 221 can define downstream chamber portion 238, socket 240, and apertures 244. Apertures 244 can be formed in pulse engine projection 221 and can be in communication with flow path 246 and downstream chamber portion 238. Pulse engine projection 221 can define open seat 250. Pulse engine projection 221, in some embodiments, can be formed integrally with pulse engine electrode 217. Thus, pulse engine projection 221 can be made from the same material as pulse engine electrode 217 which can be a conductive and corrosion resistant metal in some embodiments.

Handpiece cap 219 can define upstream chamber portion 237 and closed seat 248. In conjunction with pulse engine projection 221, handpiece cap 219 can define flow path 246 including a 90 degree turn adjacent to, and downstream from, flow control member 232. Handpiece cap 219 can couple to, and seal against, pulse engine projection 221 at coupling interface 253 which can include threads or other features for this purpose. Together, handpiece cap 219 and pulse engine projection 221 can retain flow control member 232 in valve chamber 233 while allowing flow control member 232 to move between its open and closed positions. Thus, check valve 230 of handpiece 214 can prevent flow through flow path 246 when flow control member 232 is in its closed position and can allow flow through flow path 246 when flow control member 232 is in its open position. By moving between its open and closed positions, flow control member 232 can determine whether check valve 130 is open or closed.

Embodiments provide advantages over previously available handpieces. Various embodiments provide handpiece check valves which can crack open substantially without an applied positive differential pressure. Embodiments provide check valves with fewer moving parts than previously available. Hence, embodiments provide handpieces with higher reliability than previously available handpieces.

Although embodiments have been described in detail herein, it should be understood that the description is by way of example only and is not to be construed in a limiting sense. It is to be further understood, therefore, that numerous changes in the details of the embodiments and additional embodiments will be apparent, and may be made by, persons of ordinary skill in the art having reference to this description.

It is contemplated that all such changes and additional embodiments are within scope of the claims below and their legal equivalents.

What is claimed is:

1. A handpiece comprising:
a body defining a chamber with upstream and downstream portions and a first flow path between the upstream and downstream chamber portions;
an inlet port of the body coupled to the upstream chamber portion;
a pulse engine coupled to the downstream chamber portion;
an outlet port of the body coupled to the pulse engine; and
a spring-less flow control member movable between open and closed positions between the upstream and downstream chamber portions, wherein the first flow path is configured to flow around the flow control member when the flow control member is in the open position;
wherein the body further defines a second flow path between the downstream chamber portion and the flow control member which is less restrictive than the first flow path and further wherein, in the closed position, flow from the inlet port tends to move the member to the open position thereby allowing flow through the first flow path, and in the open position, a pressure increase from the pulse engine traveling along the second flow path tends to move the flow control member to the closed position before fluid back flows through the first flow path and around the flow control member;
wherein the second flow path has a greater diameter than the first flow path throughout a region of the second flow path between the flow control member and a junction of the first flow path and the second flow path.

2. The handpiece of claim 1 wherein the flow control member is spherical.

3. The handpiece of claim 1 further comprising an insert defining at least a portion of the chamber and at least a portion of the second flow path.

4. The handpiece of claim 1 wherein the open and closed positions are about 0.001" to about 0.010" apart.

5. The handpiece of claim 1 wherein the open and closed positions are about 0.002" to about 0.003" apart.

6. The handpiece of claim 1 wherein the body has a longitudinal axis and wherein the flow control member moves between the open and closed positions in a direction parallel to the longitudinal axis.

7. The handpiece of claim 1, wherein the first flow path includes at least one portion that forms an angle with the second flow path and wherein the second flow path is straight.

8. The handpiece of claim 1, wherein the first flow path turns at least twice while the second flow path does not turn.

9. A handpiece comprising:
a body defining a chamber with upstream and downstream portions and a first flow path between the upstream and downstream chamber portions;
an inlet port of the body coupled to the upstream chamber portion;
a pulse engine coupled to the downstream chamber portion;
an outlet port of the body coupled to the pulse engine; and
a spring-less flow control member movable between open and closed positions between the upstream and downstream chamber portions, wherein the first flow path is configured to flow around the flow control member when the flow control member is in the open position;
wherein the body further defines a straight second flow path between the downstream chamber portion and the flow control member and further wherein, in the closed position, flow from the inlet port tends to move the member to the open position thereby allowing flow through the first flow path, located around the flow control member, and in the open position, a pressure increase from the pulse engine traveling along the second flow path tends to move the flow control member to the closed position before fluid back flows through the first flow path and around the flow control member;

wherein the second flow path has a greater diameter than the first flow path throughout a region of the second flow path between the flow control member and a junction of the first flow path and the second flow path.

10. The handpiece of claim 9 wherein the flow control member is spherical.

11. The handpiece of claim 9 further comprising an insert defining at least a portion of the chamber and at least a portion of the second flow path.

12. The handpiece of claim 9 wherein the open and closed positions are about 0.001" to about 0.010" apart.

13. The handpiece of claim 9 wherein the open and closed positions are about 0.002" to about 0.003" apart.

14. The handpiece of claim 9 wherein the body has a longitudinal axis and wherein the flow control member moves between the open and closed positions in a direction parallel to the longitudinal axis.

15. The handpiece of claim 9, wherein the first flow path includes at least one portion that forms an angle with the second flow path and wherein the second flow path is straight.

16. The handpiece of claim 9, wherein a pressure increase traveling through the first flow path turns at least twice while a pressure increase traveling through the second flow path does not turn.

17. The handpiece of claim 9, wherein at least a portion of the fluid flows past an entrance to the first flow path prior to traveling through a portion of the second flow path, that does not overlap the first flow path, and into contact with the flow control member to urge the flow control member into the closed position.

\* \* \* \* \*